United States Patent [19]

Hoerman

[11] Patent Number: 4,906,455
[45] Date of Patent: Mar. 6, 1990

[54] METHOD FOR TREATING XEROSTOMIA EMPLOYING CHEWING GUM CONTAINING RELATIVELY INSOLUBLE, HYDROPHOBIC, FOOD-GRADE ORGANIC ACID

[75] Inventor: Kirk C. Hoerman, Lake Forest, Ill.
[73] Assignee: Wm. Wrigley Jr. Company, Chicago, Ill.
[21] Appl. No.: 306,626
[22] Filed: Feb. 3, 1989

Related U.S. Application Data

[63] Continuation-in-part of Ser. No. 182,476, Apr. 15, 1988, abandoned.

[51] Int. Cl.$^4$ .............................................. A61K 9/68
[52] U.S. Cl. ....................................... 424/48; 514/440
[58] Field of Search ............................ 424/48; 524/440

[56] References Cited

U.S. PATENT DOCUMENTS

| | | | |
|---|---|---|---|
| 2,812,256 | 11/1957 | Nerfin | 99/135 |
| 3,151,028 | 9/1964 | Hay et al. | 167/93 |
| 3,632,358 | 1/1972 | Echeandia et al. | 99/135 |
| 4,064,274 | 12/1977 | MacKay et al. | 426/3 |
| 4,085,227 | 4/1978 | MacKay et al. | 426/3 |
| 4,088,788 | 5/1978 | Ream et al. | 426/3 |
| 4,151,270 | 4/1979 | Ream et al. | 426/3 |
| 4,233,288 | 11/1980 | Cornell | 424/48 |
| 4,400,372 | 8/1983 | Muhler et al. | 424/48 |
| 4,479,969 | 10/1984 | Bakal et al. | 426/3 |
| 4,568,537 | 2/1986 | Hoerman | 424/48 |
| 4,768,238 | 9/1988 | Kleinberg et al. | 4/258 |

OTHER PUBLICATIONS

G. Anneroth et al., Effect of Saliva Stimulants (Hybrin (R) and Malic Acid) on Cervical Root Surfaces in Vitro, Scand. J. Res., 88, 214–218, (1980).
C. M. Christensen et al., Effects of Pharmaologic Reductions in Salivary Flow on Taste Thresholds in Man, Arch. Oral Biol., 29, 17–23, (1984).
C. Dawes, Effects of Diet on Salivary Secretion and Composition, J. Dent. Res., 49, 1263–73, (1970).
E. J. Edmonds et al., Replacement Therapy in a Dry Mouth Patient: A Review, J. Hosp. Dent. Pract., 14, 30–34, (1980).
K. Hoerman et al., Gas Analysis of Saliva after Stimulation by Adipic Acid Slowly Released from Chewing Gum, J. Dent. Res., 64, 327, No. 1371, (1985), (Abstract Only).
K. C. Hoerman et al., Macromolecular Effects on the Titration Curves of Parotid Gland Fluid, J. Dent. Res., 47, 74–82, (1968).
G. N. Jenkins, "Salivary Effects on Plaque pH", 307–22, in I. Kleinberg et al., eds., Saliva and Dental Caries, (1979).
C. J. Kleber et al., Changes in Salivary pH after Ingestion of Sorbitol Tablets containing Various Food Acidulants, J. Dent. Res., 58, 1564–65, (1979).
R. J. Mathew et al., Xerostomia and Sialorrhea in Depression, Am. J. Psychiatry, 136, 1476–77, (1979).
J. R. McClelland, The Influence of Various Stimuli upon Human Saliva, Am. J. Physiol., 63, 127–41, (1922).
C. Nevin et al., Slow Release of Adipic Acid from Chewing Gum: Effects on Salivary Flow and Volume, J. Dent. Res., 64, 327, No. 1370, (1985), (Abstract Only).
E. Newbrun, Xerostomia, Oral Surg., 51, 262, (1981).
J. M. Poland, Xerostomia in the Oncologic Patient, Am. J. Hospice Care, 31–33, (May/Jun. 1987).
G. I. Roth et al., Oral Biology, Chap. 8, ("Salivary Glands and Saliva"), 196–236; Chap. 9 (Drugs: Salivary Excretion and Oral Side Effects), 239–52, (1981).
J. J. Sciubba, The Patient at Risk: Dry Mouth, J. Hosp. Dent. Pract., 14, 20, (1980).
A. Spielman et al., Xerostomia—Diagnosis and Treatment, Oral Surg., 51, 144–47, (1981).
A. Spielman, Reply, Oral Surg., 52, 263, (1982).

Primary Examiner—Shep K. Rose
Attorney, Agent, or Firm—Willian Brinks Olds Hofer Gilson & Lione

[57] ABSTRACT

A method for treating xerostomia, or dry mouth, not caused by exercising, employs a specially formulated chewing gum. The method involves chewing a sugarless gum which contains a relatively insoluble, hydrophobic, food-grade organic acid, such as adipic acid. Chewing the gum gradually releases the acid at a desirable linear rate over a period of about 20 to 30 minutes. Slow release of the acid from the gum results in an increase in salivary flow rate in xerostomia non-exercising patients having decreased salivary gland function.

13 Claims, No Drawings

4,906,455

METHOD FOR TREATING XEROSTOMIA EMPLOYING CHEWING GUM CONTAINING RELATIVELY INSOLUBLE, HYDROPHOBIC, FOOD-GRADE ORGANIC ACID

CROSS-REFERENCE TO RELATED APPLICATION

This is a continuation-in-part of copending application Ser. No. 07/182,476, filed April 15, 1988 and now abandoned.

BACKGROUND OF THE INVENTION

Xerostomia, or dry mouth, is a generally subjective condition characterized by insufficient intraoral salivary secretion. The word "xerostomia" designates a symptom (dry mouth) rather than a particular ailment causing the symptom, but the condition usually results as a side effect from use of certain drugs or from radiation therapy as a cancer treatment, which in some cases co-incidentally damages the salivary glands. As used herein, "xerostomia" designates a condition in a patient having salivary glands with decreased salivary gland function, for example, due to permanent damage or as a side effect to drug therapy, which patient, however, still has some rudimentarily functioning salivary glands.

R.L. Ream et al. U.S. Pat. No. 4,151,270, issued April 24, 1979, and assigned to the Wm. Wrigley Jr. Company, discloses a chewing gum composition for use by athletes and other persons to stimulate salivation while exercising, comprising 3 percent by weight of an organic acid and fructose.

K.C. Hoerman et al. U.S. Pat. No. 4,568,537, issued February 4, 1986, and assigned to the Wm. Wrigley Jr. Company, discloses a range of dental health gum compositions which are useful in preventing tooth demineralization and in providing tooth remineralization. These gum compositions contain a relatively insoluble, hydrophobic, food-grade organic acid, such as adipic acid.

SUMMARY OF THE INVENTION

It has been found that chewing, by a non-exercising zerostomia patient having decreased salivary gland function, i.e. while not exercising and not having recently increased mouth dryness by exercising, for a period of at least about 20 minutes, of a sugar gum or a sugarless gum which contains a relatively insoluble, hydrophobic, food-grade organic acid having a water solubility of less than 20.0% by weight at 37° C. or a degree of hydrophobicity sufficient for retention of the acid in a non-polar chewing gum base, yet releasable therefrom over an extended period of time during chewing of the gum, preferably adipic acid, results in an increase in salivary flow rate. Chewing of the gum effects a gradual release of the acid from the gum at a desirably linear rate over a period of about 20 to 30 minutes during which the acid is effective to stimulate saliva at a flow rate greater than that experienced during chewing a non-acidulated chewing gum. Gradual release of the hydrophobic acidulant from the gum stimulates salivation at a maximum rate for a prolonged period of time.

Thus, the present invention utilizes acids in a safe, natural system for treating zerostomia in an enjoyable manner and at a low cost.

DETAILED DESCRIPTION

The present invention stimulates salivary flow in xerostomia patients. As is well known, salivation is an important physiological function which has several benefits in addition to those relating to digestion.

An obvious benefit is alleviating the discomfort which results from a dry mouth.

Another benefit is the washing of tooth enamel surfaces and their surrounding soft tissues or gums. This washing provides a preventive effect against disease in direct relation to the rate of salivary flow from the four major salivary glands which empty into the human mouth under various stimulations.

Other beneficial effects of salivation arise from the action of the 1.0% dissolved constituents which exist in saliva, which is typically 99.0% water. Proteins make up about 0.3% of such dissolved constituents and function to degrade starches and other substances in the mouth by way of enzymic actions in preparation for digestion. Such proteins assist in the neutralization of acids produced in the mouth or introduced through foods and beverages. For example, certain proline rich protein (PRP) molecules in saliva are believed to bind to tooth surfaces forming a protective layer, while others in the mouth act to aggregate and clear acid-producing bacteria and which PRP molecules are therefore thought to be anticariogenic.

Inorganic constituents such as calcium, phosphorus, bicarbonate and other electrolytes occur in saliva and make up the remaining 0.7% of the solid constituents. Calcium and phosphorous are present at levels which saturate the saliva solution in order to prevent dissolution of tooth enamel under normal circumstances and effect remineralization of early decayed enamel surfaces.

In normal individuals, resting or unstimulated salivary flow is typically less than 0.1 ml/minute. Non-resting or stimulated salivary flow can occur due to aromas, flavors, tastes (either sweet, sour, salty or bitter) and masticatory actions. Chewing alone can cause a four fold increase in the flow rate. Sour foods are far more effective in increasing flow rate and volume, often as much as ten times the resting flow.

Saliva from stimulated glands differs qualitatively from that derived from resting glands, the most dramatic difference being in the pH, which varies from the acidic pH level of 5.5 to the more basic pH level of 7.8 during maximum saliva flow due to the higher level of bicarbonate ion then present in the fluid. The concentration of calcium, phosphorous and other electrolytes also rises when the saliva flow is at an increased rate. After maximum flow is established, the concentration of salivary electrolytes continues to rise and may not achieve a steady state even after 15 minutes of stimulated flow.

In the present invention, the concentration of bicarbonate in saliva (as indicated by saliva pH) increases as the rate of flow of the saliva from the salivary glands increases, as described in greater detail in U.S. Pat. No. 4,568,537, the disclosure of which is incorporated by reference.

The present invention achieves the desirable effect of a prolonged stimulation of saliva over an extended time period, on the order of 20 to 30 minutes, through a slow release of a sparingly soluble food acidulant from chewing gum base during chewing of the gum. Such a release characteristic produces a quantity of bicarbonate buffer which raises the pH of the saliva. Unlike soluble acidulants, relatively insoluble hydrophobic acids having a water solubility of less than about 20% by weight at 37° C., preferably less than 7%. Examples of suitable acidulants for use in the present invention include adipic, fumaric, succinic, suberic, sebacic, azelaic and pimelic acids. These acids are persistent in the gum base during chewing and do not produce a drastic drop in the pH of saliva. For this reason, higher acid levels can be used without producing excessive and unpleasant tartness. The chewing of the gum brings about a slow, linear (non-exponential) release of the acid from the gum base such that a slowly decreasing concentration of acid in the gum base occurs as opposed to the rapidly declining exponential release of soluble or hydrophilic food acidulants. Further, as would be expected from the nearly linear release of adipic acid from the gum, it has been found that the gum, throughout the 20-30 minute period of acid release, promotes a more nearly constant stimulation of parotid salivary flow as compared with gums containing rapidly dissipated acidulants such as citric acid which cause an initial stimulation of the saliva flow rate followed by an abrupt exponential decrease in rate. As explained more fully in U.S. Pat. No. 4,568,537, gum containing 3% adipic acid stimulates nearly twice as much saliva as similar gum containing 3% citric acid.

The use of chewing gum in the present invention which effects a slow, controlled release of acid from the gum is to be contrasted with the use of other delivery methods such as hard candy or chewing gum containing a rapidly released acid such as citric, malic, or tartaric acid. In the case of hard candy, high concentrations of acid overpowering the natural buffer capacity in saliva are delivered at a steady rate for a short period of time in combination with a high sugar content. Similarly, gum containing a rapidly-released acidulant also produces an abrupt drop in pH of the oral environment sometimes in combination with high sugar levels. Thus, the use of hard candy or chewing gums containing rapidly-dissipated acidulants, as contrasted with the present invention, enhances cariogenicity in the oral environment.

During the 20 to 30 minute acid release period in the present invention, the sustained acid and resulting taste stimulus is effective to increase saliva to a flow rate greater than that experienced during chewing a non-acidulated chewing gum. The result is a proportional increase in dental washing, a proportional increase in the concentration of salivary electrolytes and basic proteins and, most importantly, a proportional increase in the concentration of natural salivary bicarbonate which, upon neutralizing the gum acidulant, results further in an elevation of the salivary pH above that of unstimulated saliva.

The gum for use in the method of the present invention comprises gum base, a sugar or sugarless sweetener, flavoring and the relatively insoluble foodgrade organic acid in an amount ranging from about 1.0 to about 6.0% by weight of the chewing gum composition.

The preferred food-grade acid is adipic acid, in an amount ranging from about 2.0% to about 3.5% by weight (optimum amount of about 3.0% by weight) of the chewing gum composition. A second preference is fumaric acid in an optimum amount of about 4.0% by weight.

The sugar sweetener in the chewing gum for use in the present invention, if used, can be any sugar commonly used in chewing gum such as sucrose, dextrose, fructose, corn syrup, or the like, or a combination of such sugar sweeteners.

The sugarless sweetener in the chewing gum for use in the present invention, if used, can be a water-soluble bulking agent present in an amount ranging from about 30% to about 65% by weight of the entire chewing gum composition and may comprise a sugar alcohol or mixtures thereof selected from the group consisting of sorbitol, mannitol or xylitol. The sugarless sweetener may be an artificial high-potency sweetener, that is, one having a sweetness greater than 20 times that of sucrose such as saccharin, thaumatin, a cyclamate or acesulfame K. However, one preferred such sweetener is the dipeptide sweetener aspartame (L-aspartyl-L-phenylalanine methyl ester, originally disclosed in U.S. Pat. Nos. 3,492,131 and 3,642,491, issued January 27, 1970 and February 25, 1972, to Schlatter) which is used in an amount of about 0.025% to about 2.0% but preferably about 0.1% by weight of the chewing gum composition. The bulking agent may comprise a partially indigestible and non-cariogenic carbohydrate such as polydextrose.

The gum bases of the chewing gum for use in the present invention should be free of calcium carbonate or other alkaline fillers which tend to neutralize the food acid component. A preferred filler for the gum bases of the chewing gum for use in the present invention is talc, which does not react with acids.

EXAMPLE 1

An adipic acid-containing chewing gum was produced according to the following formulation:

| Ingredient | Percent by Weight |
| --- | --- |
| Sorbitol | 47.70 |
| Gum Base | 24.75 |
| Glycerin | 15.30 |
| Mannitol | 8.00 |
| Adipic Acid | 3.00 |
| Lemon Flavor | 1.00 |
| Aspartame | 0.25 |
| | 100.00 |

The adipic acid-containing chewing gum was given to a patient who suffered from xerostomia induced by radiation therapy for cancer, and not caused by exercising. The patient characterized his dry mouth as a "pretty bad problem" after eating and between meals and after arising in the morning, and as a "moderate problem" after taking medication; and indicated that dry mouth was almost always present. He indicated that dry mouth caused a moderate amount of tooth decay, and that the fact that nothing helped his dry mouth to get better was a "pretty bad problem". He had previously found drinking water to be very helpful in relieving dry mouth, but chewing gum and toothbrushing to be only moderately helpful.

The patient chewed the adipic acid-containing chewing gum while experiencing xerostomia not caused by exercising. After chewing the gum for 20 minutes, the patient indicated that the gum was effective to help his dry mouth, that he experienced no unpleasant sideeffects, and that the relief from dry mouth lasted more than 10 minutes after he chewed the gum. The gum relieved his dry mouth, making his mouth more comfortable and his breath fresher.

A month after using a total of 20 sticks of the gum, the patient was asked his impression of it. He indicated it has been very helpful in relieving his dry mouth condition, and inquired as to its commercial availability.

EXAMPLE 2

A gum suitable for use in the method of the present invention can be made according to the following formulation:

| Ingredient | Percent by Weight |
| --- | --- |
| Sorbitol | 39.41 |
| Gum Base | 26.91 |
| 70% Sorbitol Solution | 17.31 |
| Mannitol | 12.01 |
| Adipic Acid | 2.00 |
| Lemon Flavor | 1.56 |
| Glycerine | 0.80 |
| | 100.00 |

This gum exhibits a mild, pleasant and long-lasting tartness which compliments the lemon flavor.

EXAMPLE 3

As aspartame gum preferred for use in the present invention can be made according to the following formulation:

| Ingredient | Percent by Weight |
| --- | --- |
| Sorbitol | 38.31 |
| Gum Base | 26.91 |
| 70% Sorbitol Solution | 17.31 |
| Mannitol | 12.01 |
| Adipic Acid | 3.00 |
| Lemon Flavor | 1.56 |
| Glycerine | 0.80 |
| Aspartame | 0.10 |
| | 100.00 |

The aspartame provides improved sweetness for the chewing gum and the adipic acid contributes to the stabilization of the aspartame.

EXAMPLE 4

Another gum suitable for use in the present invention can include fumaric acid in the following formulation:

| Ingredient | Percent by Weight |
| --- | --- |
| Sorbitol | 37.97 |
| Gum Base | 26.91 |
| 70% Sorbitol Solution | 17.31 |
| Mannitol | 12.01 |
| Fumaric Acid | 4.00 |
| Apple Flavor | 1.00 |
| Glycerine | 0.80 |
| | 100.00 |

EXAMPLE 5

Another gum suitable for use in the present invention can include sucrose as the sweetener:

| Ingredient | Percent by Weight |
| --- | --- |
| Sucrose | 62.35 |
| Gum Base | 20.92 |
| Corn Syrup | 12.76 |
| Adipic Acid | 3.00 |
| Mixed Fruit Flavor | .87 |
| Color | 0.10 |
| | 100.00 |

What is claimed is:

1. A method for treating xerostomia in a non-exercising patient having functioning salivary glands with decreased salivary gland function, comprising the step of chewing, by the xerostomia patient, for a period of at least about 20 minutes, a gum whose essential salivary flow rate increasing agent, effective to stimulate saliva at a maximum rate for a prolonged period of time, consists essentially of a food-grade organic acid selected from the group consisting of adipic, fumaric, succinic, suberic, sebacic, azelic and pimelic acids, in an amount ranging from about 1.0% to about 6.0% by weight of the chewing gum composition, the acid having a water solubility of less than about 20.0% by weight at 37° C. or a degree of hydrophobicity sufficient for retention of the acid in a non-polar chewing gum base yet releasable therefrom over an extended period of time during chewing of the gum, the acid being released during chewing of the gum to stimulate saliva at a flow rate greater than that experienced during chewing a non-acidulated chewing gum; said gum being free of rapidly released and cariogenic citric, malic or tartaric acid, as well as free of calcium carbonate or other alkaline fillers which tend to neutralize the food acid.

2. The method of claim 1 wherein the organic acid is adipic acid.

3. The method of claim 2 wherein the adipic acid is present in an amount ranging from about 2.0% to about 3.5% by weight of the chewing gum composition.

4. The method of claim 1 wherein the organic acid is fumaric acid.

5. The method of claim 4 wherein the fumaric acid is present in an amount of about 4.0% by weight of the chewing gum composition.

6. The method of claim 1 wherein the organic acid has a water solubility of less than about .7.0% by weight at 37° C.

7. The method of claim 1 wherein the organic acid is released from the gum at a non-exponential rate over a time period of about 20 to 30 minutes.

8. The method of claim 1 wherein the gum is a sugarless gum, and wherein a sweetening ingredient of the sugarless gum is a sugar alcohol or a combination of sugar alcohols.

9. The method of claim 8 wherein the sugar alcohol or combination of sugar alcohols is selected from the group consisting of sorbitol, mannitol and xylitol, and mixing thereof.

10. The method of claim 1 wherein the gum is a sugarless gum, and wherein a sweetening ingredient of the sugarless gum is a sugarless high-intensity sweetener.

11. The method of claim 10 wherein the sugarless high-intensity sweetener is selected from the group consisting of aspartame, saccharin, thaumatin, a cyclamate or acesulfame K.

12. The method of claim 1 wherein the gum is a sugar gum, and wherein a sweetening ingredient of the sugar gum is selected from the group consisting of sucrose, dextrose, fructose, corn syrup and mixtures thereof.

13. A method for treating xerostomia in a non-exercising patient having functioning salivary glands with decreased salivary gland function, comprising the step of chewing, by the xerostomia patient, for a period of at least about 20 minutes, a gum whose essential salivary flow rate increasing agent, effective to stimulate saliva at a maximum rate for a prolonged period of time, consists essentially of a hydrophobic food-grade organic acid selected from the group consisting of adipic, fumaric, succinic, suberic, sebacic, azelic and pimelic acids, the acid having a water solubility of less than about 20.0% by weight at 37° C.; said gum being free of rapidly released and cariogenic citric, malic or tartaric acid, as well as free of calcium carbonate or other alkaline fillers which tend to neutralize the food acid.

* * * * *